United States Patent [19]

Kimura et al.

[11] Patent Number: 4,877,784

[45] Date of Patent: Oct. 31, 1989

[54] HISTIDYLPROLINEAMIDE DERIVATIVES

[75] Inventors: Kiyoshi Kimura, Yasuokatermachi; Takashi Ogasawara, Ugi; Takeshi Mushiroi, Kyoto, all of

[73] Assignee: Nippon Shinyaku Co., Ltd., Japan

[21] Appl. No.: 209,287

[22] Filed: Jun. 20, 1988

[30] Foreign Application Priority Data

Jun. 19, 1987 [JP] Japan .................................. 62-154237

[51] Int. Cl.$^4$ ............................................. A61K 31/54
[52] U.S. Cl. .................................................. 514/227.8
[58] Field of Search ........................................ 514/222

[56] References Cited

FOREIGN PATENT DOCUMENTS

| | | |
|---|---|---|
| 853444 | 4/1976 | Belgium . |
| 2449167 | 4/1976 | Fed. Rep. of Germany . |
| 2615455 | 4/1976 | Fed. Rep. of Germany . |
| 1564078 | 4/1980 | United Kingdom . |

OTHER PUBLICATIONS

Chem. Abst. 98-28331f (1983).

Abstract of article in Noo to Shinkei 35, 501–504 (1983) with information sheet re "Dn-1417".
Abstract of South African Pat. No. 75-5956.

*Primary Examiner*—Stanley J. Friedman
*Attorney, Agent, or Firm*—Jacobs & Jacobs

[57] ABSTRACT

A compound of the formula I

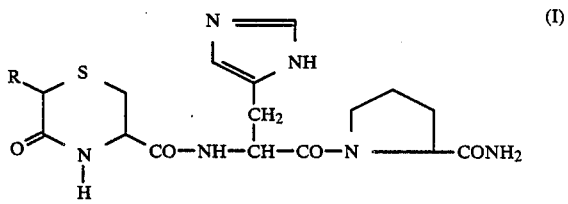

wherein R is lower alkyl has been found to have antiepileptic properties and to be useful in the treating of epilepsy in humans and animals. Pharmaceutical compositions and methods of treatment are described herein.

6 Claims, No Drawings

HISTIDYLPROLINEAMIDE DERIVATIVES

The present invention is concerned with histidylprolineamide derivatives. More particularly, the present invention relates to such derivatives which have been found to be useful as antiepileptic agents. Intractable epilepsy exhibits various serious symptoms. Efforts have been under way for many years to develop drugs useful in the treatment of epilepsy. In recent years, some antiepileptics such as phenytoin have been developed and used to control epileptic fits and seizures. The fit associated with epilepsy is inhibited by continued administration of hypnotics such as phenobarbital. However, because the cause of epilepsy is not simple and well understood, drugs useful for effecting a recovery from epilepsy have not as yet been found.

Inanaga et al (The Kurume Medical J., 28, 201, 1981) reported on the effectiveness of TRH (Thyrotropin-Releasing Hormone) on intractable epilepsy. Primarily, TRH was considered to be a hormone which controlled the release of thyrotropin (TSH) in the mammalian pituitary gland. However, according to recent studies, (see Ann. Rev. Pharmacol. Toxicol. 26, 311–322, 1986) TRH has been found to regulate not only release of TSH but to act on various neurones because of its wide distribution in the central nervous system.

Though it has been known that TRH exhibits various useful actions and can be effective as an antiepiletic agent, it is also known that TRH is metabolized relatively easily in vivo and its penetration and absorption into the brain is, therefore, very poor. Moreover, the action of TRH is not as potent as initially expected by research workers in the field. Thus, there remains a demand for a potent and effective effective anti-epileptic activity.

Moreover, because of the relatively rapid metabolism of TRH, it is not suitable for oral administration. When TRH or TRH-related compounds are administered systemically, the duration of their effect is short and the effective dosage is rather limited. Experiments have shown that there is no dose dependency (thus, the effect does not increase in proportion to an increase in dose) and consequently, the development of such drugs has not shown promise (see Kiyoshi Morimoto, et al:Noo to Shinkei, 35, 501–504, 1983).

Histidylprolineamide derivatives including the compounds of the present invention are known to have CNS action and to be useful as psychostimulants and antidepressants-see DE 2,449,167 and DE 2,615,455 (BE 853,444), and have been studied because of their prominent pharmacological action. Attempts have been made to use them for the treatment of neuronal damage after brain injury for example sectional paralysis resulting from bone-marrow trauma and central nervous system dysfunctions resulting from brain trauma (see Japanese Laid Open Application 61/172828 and DE 3502-041A). However, no one has as yet studied the compounds of the present invention in relation to specified pharmacological action so that they can be used as therapeutic substances.

The present inventors have discovered that histidylprolineamide derivatives of the formula I

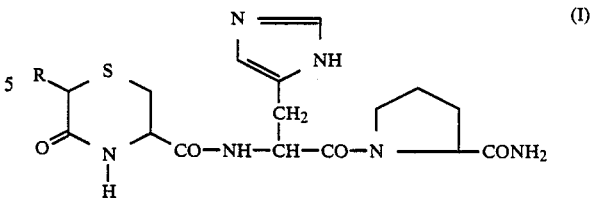

wherein R is lower alkyl exhibit quite excellent antiepilptic action on administration to mammalian animals as compared with TRH. Even upon oral administration, the compounds of the present invention exhibit marked antiepileptic action and this represents a substantial advance in the art.

The compounds of the present invention have four asymmetric carbon atoms. The present invention thus includes all of the optical isomers.

According to one embodiment of the present invention, R is methyl, ethyl or propyl. Representative compounds of the present invention are :

6-methyl-5-oxo-3-thiomorpholinylcarbonylhistidyl-prolineamide.

6-ethyl-5-oxo-3-thiomorpholinylcarbonylhistidyl-prolineamide.

6-propyl-5-oxo 3-thiomorpholinylcarbonylhistidyl-prolineamide.

The pharmacological activity and toxicity of the compounds of the present invention are illustrated in detail below. In the following test, (3R,6R)-6-methyl-5-oxo-thiomorpholinycarbonylL-histidyl-L-prolineamide was used as the representative compound of the present invention.

The animals used were Wistar strain male rats (body weight 240–280 g). They were anesthetized by the intraperitoneal injection of 40–50 mg/kg of sodium pentobarbital. Then the head of the rat was fixed on a stereotaxic apparatus, and silver ball electrodes were placed on the surface of the motor cortex. Stainless steel bipolar electrodes were implanted into the ipsilateral amygdaloid nucleus according to the brain atlas of Konig and Klippel (see Robert E. Krieger Publishing Co., Inc., Huntington, N.Y., 11743, 1970). Leading wires from the electrodes were connected with each pin of the small socket and were fixed on the cranium using dental cement. The rat was allowed to completely recover from the surgery. Then electrical stimulation was started to develop the kindling.

The electrical stimulation of the amygdaloid nucleus was applied every 24 hours by delivering rectangular pulses of 1 mesc duration at 60 Hz for 1 second every day. The initial stimulating current was 200 $\mu A$ and, depending on the degree of the development of kindling, it was increased with a 50 $\mu A$ step. The degree of convulsion was evaluated with the scoving system as given below (Table 1) depending upon the epileptic behavior (see Classification according to Racine; Racine, et al: Clin. Neurophysiol., 32, 281, 1972). Durations of the afterdischarges were determined from the chart which records the EEG. Rats in which the symptoms of the fifth grade were observed for three consecutive days and the duration of the afterdischarges remained constant were used for the experiments.

The compound of the present invention and TRH were administered intraperitoneally 15 and 20 minutes respectively before the electrical stimulation. When the drugs were repeatedly administered to the same rat, at least five days intervals were set.

TABLE 1

Scoring systems evaluating for Epileptic Behavior

| Score | Epileptic Behavior |
|---|---|
| 1 | Twitching of the mouth and face |
| 2 | Nodding of head |
| 3 | Clonic spasm of forefoot |
| 4 | Rearing with hindfoot accompanied by clonic convulsion |
| 5 | Falling down accompanied by general convulsion |

The results are set forth below in Table 2.

TABLE 2

| Agent Used | Dose (mg/kg) | Nos of Animals | Duration of Afterdischarge (% Change) | Average Degree of Epilepsy |
|---|---|---|---|---|
| Physiological Saline | — | 6 | 106.7 ± 3.8 | 5.0 |
| The Present Invention Compound | 0.01 | 5 | 94.1 ± 14.7 | 5.0 |
|  | 0.03 | 4 | 82.6 ± 7.8* | 4.0++ |
|  | 0.1 | 6 | 78.7 ± 16.8 | 3.3++ |
| TRH | 1 | 4 | 104.4 ± 3.7 | 5.0 |
|  | 3 | 4 | 112.7 ± 14.0 | 5.0 |
|  | 10 | 4 | 100.6 ± 10.0 | 5.0 |

*$p < 0.05$ (t-test)
++$p < 0.01$ (Wilcoxon's rank sum test)

The compound of the present invention decreased duration of afterdischarge at dosages higher than 0.01 mg/kg, in a dose dependent manner. At doses higher than 0.03 mg/kg, it decreased epileptic behavior in a dose dependent manner. By contrast, in the case of TRH, no inhibitory effects on afterdischarge were observed nor were any effects on epileptic behavior observed at the dosages administered. From these results, it is apparent that the compound of the present invention is effective to treat intractable epilepsy including Lennox-Gastaut epilepsy for which TRH is said to be somewhat effective.

The toxicity of the compounds of the present invention was determined in the following manner. The representative compound of the present invention was administered intravenously and orally to male mice and the toxic symptoms were observed for seven days. Following intravenous administration of 1000 mg/kg, no deaths were observed in animals receiving the compound of the present invention and no toxic symptoms were observed. On oral administration, there was neither death nor toxic symptoms observed at a dose of 5000 mg/kg. This is clear evidence that the compounds of the present invention are safe.

The compounds of the present invention may be administered per se or may be formulated into pharmaceutical compositions containing pharmaceutically acceptable nontoxic carriers.

When the compounds of the present invention are administered to humans and animals as a pharmaceutical composition such compositions contain, for example, 0.0001% to 1.2% by weight, for compositions in injectable administration form. The range for tablets would be 0.0001 to 2% preferably, 0.01% to 1.0% for injection and 0.001 to 1.0% for tablets of active ingredient in combination with a pharmaceutically acceptable carrier.

The compounds of the present invention may be given orally, parenterally, topically (through the skin) or rectally. They are of course administered or applied in forms suitable for the particular administration or application route. For example, oral administration would be by tablets or capsules; parenteral by injection, infusion or inhalation; topical by lotion or ointment; and rectal by suppositories. Oral administration forms are particularly preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules, suspensions, syrups and the like.

Powders are prepared by comminuting the compound to a suitably fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as carboxymethylcellulose, carboxymethylcellulose calcium, substituted hydroxypropyl cellulose, agar-agar, calcium carbonate or sodium carbonate can also be added to improve the availability of the medicament when the capsule is ingested. When the mixture is finely powdered it may be suspended or dispersed in plant oil, polyethyleneglycol, glycerol, surface active agents and the like and then packed in gelatine sheaths to prepare soft capsules.

Tablets are formulated, for example, by preparing a powder mixture, granulating or slugging, adding a lubricant and disintegrant and compressing into tablets. A powder or pulverized mixture is prepared by mixing the compound, suitably comminuted, with a diluent or base as described above, and optionally, with a binder as carboxymethylcellulose, alginates, gelatin, or polyvinylpyrrolidone, polyvinylalcohol and the like, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen or sieve. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound.

Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethyleneglycols, cocoa butter, higher esters such as myristyl palmitate, or mixtures thereof.

Topical application forms are produced according to techniques and procedures per se known and include the usual formulating agents and additives.

In determining the dosage for treating epilepsy a number of factors such as the age of the patient, body weight, severity of condition, administration route and the like must be considered. Generally, about 0.01 to 50 mg/day may be administered to adults, preferably 0.1 to 10 mg/day for a human adult. In some cases, a lower dose is sufficient and, in some other cases, a higher dose or more doses may be necessary. The administration is preferably one to several times a day.

The compounds of the present invention may be administered alone or in combination with other drugs such as antacids, anticholinergic agents without CNS action, histamine $H_2$ antagonists and the like.

The following nonlimitative examples illustrate the preparation of pharmaceutical compositions according to the present invention.

EXAMPLE 1

(3R,6R)-6-methyl-5-oxo-3-thiomorpholinylcarbonyl-L-histidyl-L-prolineamide (4 mg), 50 mg of lactose, 22 mg of corn starch, 5.1 mg of crystalline cellulose, 3.4 mg of hydroxypropylcellulose and 0.5 mg of magnesium stearate were combined into tablets in accordance with conventional procedures.

EXAMPLE 2

(3R,6R)-6-methyl-5-oxo-3-thiomorpholinylcarbonyl-L-histidyl-L-prolineamide (4 mg), 335 mg of lactose, 144.5 mg of corn starch, 1.5 mg of aqueous silicon dioxide and 15 mg of hydroxypropylcellulose were granulated and combined into one tablets in accordance with conventional procedures.

We claim:

1. A method of treating epilepsy in humans and animals which comprises administering to a human or animal in need thereof a therapeutically effective amount of a compound of the formula I

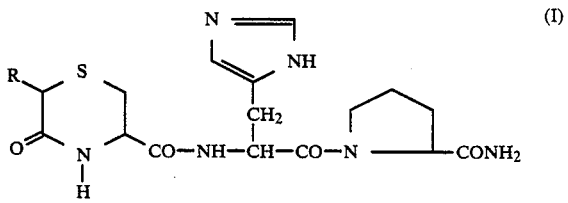

wherein R is lower alkyl, in combination with a pharmaceutically acceptably carrier.

2. A method according to claim 1 wherein R is methyl, ethyl or propyl.

3. A method according to claim 1 wherein the compound is 6-methyl-5-oxo-3-thiomorpholinylcarbonyl-histidylprolineamide.

4. A method according to claim 1 wherein the compound is 6-ethyl-5-oxo-3-thiomorpholinylcarbonylhistidylprolineamide.

5. A method according to claim 1 wherein the compound is 6-propyl-5-oxo-3-thiomorpholinylcarbonylhistidylprolineamide.

6. A method according to claim 1 wherein the compound is (3R,6R)-6-methyl-5-oxo-3-thiomorpholinylcarbonylL-histidyl-L-prolineamide.

* * * * *